United States Patent [19]

Ruoslahti et al.

[11] Patent Number: 4,661,111

[45] Date of Patent: Apr. 28, 1987

[54] POLYPEPTIDE

[75] Inventors: Erkki I. Ruoslahti, Olivenhain; Michael D. Pierschbacher, San Diego, both of Calif.

[73] Assignee: La Jolla Cancer Research Foundation, La Jolla, Calif.

[21] Appl. No.: 735,816

[22] Filed: May 17, 1985

Related U.S. Application Data

[62] Division of Ser. No. 405,239, Aug. 4, 1982, Pat. No. 4,517,686.

[51] Int. Cl.$^4$ .............. A61F 1/00; A61K 37/00; C07C 103/52; C07G 7/00
[52] U.S. Cl. ........................ 623/11; 623/66; 623/1; 623/2; 514/12
[58] Field of Search .................. 260/112.5; 3/1, 1.4; 128/1 R, 334 R; 424/177; 514/12; 623/11, 66, 1, 2

[56] References Cited

U.S. PATENT DOCUMENTS 3,717,502 2/1973 Masuhara et al. ................. 3/1.0

OTHER PUBLICATIONS

Grinnell; "The Role of Fib. in the Bioreact. of Mat. Sur.", in *Biocompatible Poly Metals and Comp.;* Technomic Co. 1983.

*Primary Examiner*—Richard J. Apley
*Assistant Examiner*—Gregory Beaucage
*Attorney, Agent, or Firm*—Irell & Manella

[57] ABSTRACT

A polypeptide having the cell-attaching activity of fibronectin. The polypeptide has 108 amino acid residues and the formula: H-Ile-Gly-Gln-Gln-Ser-Thr-Val-Ser-Asp-Val-Pro-Arg-Asp-Leu-Glu-Val-Val-Ala-Ala-Thr-Pro-Thr-Ser-Leu-Leu-Ile-Ser-Trp-Asp-Ala-Pro-Ala-Val-Thr-Val-Arg-Tyr-Tyr-Arg-Ile-Thr-Tyr-Gly-Glu-Thr-Gly-Gly-Asn-Ser-Pro-Val-Gln-Glu-Phe-Thr-Val-Pro-Gly-Ser-Lys-Ser-Thr-Ala-Thr-Ile-Ser-Gly-Leu-Lys-Pro-Gly-Val-Asp-Tyr-Thr-Ile-Thr-Val-Tyr-Ala-Val-Thr-Gly-Arg-Gly-Asp-Ser-Pro-Ala-Ser-Ser-Lys-Pro-Ile-Ser-Ile-Asn-Tyr-Arg-Thr-Glu-Ile-Asp-Lys-Pro-Ser-Gln-Met-OH. The polypeptide or a biologically active fragment thereof can be employed in the preparation of substrate designed for the attachment of cells thereto. It can be linked to the surface of a prosthetic device to particularly attract endothelial cells and fibroblastic cells.

6 Claims, No Drawings

POLYPEPTIDE

This application is a division, of application Ser. No. 405,239, filed Aug. 4, 1982, now U.S. Pat. No. 4,517,686.

This invention is directed to polypeptides related to fibronectin and more particularly to a polypeptide segment of human plasma fibronectin which interacts with cell surfaces and promotes attachment thereto.

BACKGROUND OF THE INVENTION

Fibronectin is a large glycoprotein, about 450 thousand daltons, which is composed of several apparently independent functional domains. Fibronectin was earlier discovered as a major extracellular matrix protein, and it was demonstrated that it would interact in vitro with other structural molecules, such as collagen, glycosaminoglycans, proteoglycans, fibrinogen, fibrin, and actin, as well as with cell surfaces. It was discovered that fibronectin promotes the attachment of suspended cells to collagen and also that it promotes the attachment of suspended cells directly to tissue culture substrate, independent of its binding to collagen. Accordingly, investigation continued with respect to the region of the fibronectin molecule that interacts with cell surfaces.

SUMMARY OF THE INVENTION

A polypeptide fragment of fibronectin which embodies the cell-attachment-promoting activity of fibronectin has now been isolated, purified and characterized as a polypeptide having the formula: H-Ile-Gly-Gln-Gln-Ser-Thr-Val-Ser-Asp-Val-Pro-Arg-Asp-Leu-Glu-Val-Val-Ala-Ala-Thr-Pro-Thr-Ser-Leu-Leu-Ile-Ser-Trp-Asp-Ala-Pro-Ala-Val-Thr-Val-Arg-Tyr-Tyr-Arg-Ile-Thr-Tyr-Gly-Glu-Thr-Gly-Gly-Asn-Ser-Pro-Val-Gln-Glu-Phe-Thr-Val-Pro-Gly-Ser-Lys-Ser-Thr-Ala-hr-Ile-Ser-Gly-Leu-Lys-Pro-Gly-Val-Asp-Tyr-Thr-Ile-Thr-Val-Tyr-Ala-Val-Thr-Gly-Arg-Gly-Asp-Ser-Pro-Ala-Ser-Ser-Lys-Pro-Ile-Ser-Ile-Asn-Tyr- Arg-Thr-Glu-Ile-Asp-Lys-Pro-Ser-Gln-Met-OH. This polypeptide has 108 amino acid residues, and it or a biologically active fragment thereof can be used to prepare substrata that will attach to cells. Such substrata will be useful in cell culture dishes and should also be useful for employment in medical prosthetic devices for implantation in the human body that will attract a certain type of cell to a surface.

DETAILED DESCRIPTION OF THE PREFERRED EMBODIMENTS

The nomenclature used to define the polypeptide is that specified by Schroder & Lubke, "The Peptides", Academic Press (1965) wherein, in accordance with conventional representation the N-terminus appears to the left, and the C-terminus appears to the right. Where the amino acid residue has isomeric forms, it is the L-form of the amino acid that is represented.

The invention provides a polypeptide having the following formula: H-Ile-Gly-Gln-Gln-Ser-Thr-Val-Ser-Asp-Val-Pro-Arg-Asp-Leu-Glu-Val-Val-Ala-Ala-Thr-Pro-Thr-Ser-Leu-Leu-Ile-Ser-Trp-Asp-Ala-Pro-Ala-Val-Thr-Val-Arg-Tyr-Tyr-Arg-Ile-Thr-Tyr-Gly-Glu-Thr-Gly-Gly-Asn-Ser-Pro-Val-Gln-Glu-Phe-Thr-Val-Pro-Gly-Ser-Lys-Ser-Thr-Ala-Thr-Ile-Ser-Gly-Leu-Lys-Pro-Gly-Val-Asp-Tyr-Thr-Ile-Thr-Val-Tyr-Ala-Val-Thr-Gly-Arg-Gly-Asp-Ser-Pro-Ala-Ser-Ser-Lys-Pro-Ile-Ser-Ile-Asn-Tyr-Arg-Thr-Glu-Ile-Asp-Lys-Pro-Ser-Gln-Met-OH and is intended to include fragments of the foregoing which are biologically active.

The polypeptide, or a fragment thereof, can be synthesized by any suitable method, such as by exclusively solid-phase techniques, by partial solid-phase techniques, by fragment condensation or by classical solution addition. Moreover, synthesis may be carried out by recently developed recombinant DNA techniques.

Common to chemical syntheses of peptides is the protection of the labile side-chain groups of the various amino acid moieties with suitable protecting groups which will prevent a chemical reaction from occurring at that site until the group is ultimately removed. Usually also common is the protection of an alpha-amino group on an amino acid or a fragment while that entity reacts at the carboxyl group, followed by the selective removal of the alpha- amino-protecting group to allow subsequent reaction to take place at that location. Accordingly, it is common that, as a step in the synthesis, an intermediate compound is produced which includes each of the amino acid residues located in the desired sequence in the peptide chain with various of these residues having side-chain protecting groups. These protecting groups are then commonly removed substantially at the same time so as to produce the desired resultant product following purification.

The peptides are preferably prepared using solid phase synthesis, such as that described by Merrifield, *J. Am. Chem. Soc.*, 85, 2149 (1964), although other equivalent chemical syntheses known in the art, as mentioned above, can also be used. Solid-phase synthesis is commenced from the C-terminus of the peptide by coupling a protected α-amino acid to a suitable resin, as generally set forth in U.S. Pat. No. 4,244,946, issued Jan. 21, 2982 to Rivier et al., the disclosure of which is incorporated herein by reference. Examples of syntheses of this general type are set forth in U.S. Pat. Nos. 4,305,872 and 4,316,891. Discussion of the solid-phase synthesis of a 41-residue polypeptide is set forth in *Science*, 213, 1394–1397 (September 1981) in an article by Vale et al., which refers to a more detailed discussion of the synthesis, which appears in an article by Marki et al. in *J. Am. Chem. Soc.*, 103, 3178 (1981).

In synthesizing the polypeptide, Met having its methylthiol side-chain and its α-amino group suitably protected is coupled to a chloromethylated polystyrene resin or the like. After removal of the α-amino protecting group, as by using trifluoroacetic acid in methylene chloride, the next step in the synthesis is ready to proceed. Other standard cleaving reagents and conditions for the removal of specific amino protecting groups may be used, as described in "The Peptides" identified hereinbefore.

The remaining α-amino- and side-chain-protected amino acids are then coupled stepwise in the desired order to obtain an intermediate compound connected to the resin. As an alternative to adding each amino acid separately in the synthesis, some of them may be coupled to one another prior to the addition to the solid-phase reactor. The selection of the appropriate coupling reagents is within the skill of the art.

After the desired amino acid sequence has been completed, the intermediate peptide is removed from the resin support by treatment with a reagent, such as liquid HF, which not only cleaves the peptide from the resin, but also cleaves all the remaining side-chain-protecting groups. The polypeptide can then be purified by gel permeation followed by semipreparative HPLC, as described in Rivier et al., *Peptides: Structure and Biological Function* (1979) pp. 125-128. A purity of at least 93% or higher (based upon all peptides present) is reasonably obtainable and is preferred for clinical testing and/or use. Purity of 98% is practical; however, for certain in vitro applications, lower purity may be acceptable. Accordingly, the polypeptide is considered useful when it is in substantially pure form which, for purposes of this application means at least about 50 weight percent, based upon all peptides present.

Although it is known that the entire polypeptide exhibits the desired cell-attachment activity, it is anticipated that fragments of the polypeptide will also be biologically active and will also exhibit the same, or substantially the same, cell-attaching activity, as is well known in the art of polypeptides; and accordingly, those biologically active fragments of the 108-amino-acid-residue polypeptide are considered as constituting part of the invention. The entire polypeptide or a biologically active fragment can be used as a cell-attachment protein to provide substrata to which cells will attach by treating a hydrophobic surface, such as untreated synthetic plastic resin material, e.g., nitrocellulose, or comparable material, with the polypeptide. A similar substratum for cell attachment can be generated by coupling the polypeptide covalently to a solid support, such as glass or a synthetic plastic resin or a long chain polysaccharide, such as agarose, containing a reactive group that can bind the polypeptide. This latter approach has been reduced to practice by coupling the peptide to cyanogen bromide-activated agarose beads (sold under the trademark Sepharose by Pharmacia Fine Chemicals, Uppsala,, Sweden), sterilizing the beads by autoclaving and thereafter showing that the polypeptidecoating induces attachment of cells to the beads in a concentration greater than can be obtained by passive absorbtion.

It is expected that such substrata will be useful in cell cultures where it is desirable to ensure proper attachment of the cells. Attachment proteins, such as fibronectin, have been shown to be important for the growth of many types of cells in vitro. Chemically defined media are often supplemented by attachment proteins (Barnes and Sato, *Cell* 22:649-655, 1980). Coating of the culture substratum with the cell-attachment polypeptide would obviate the use of fibronectin in the medium, thus providing better defined conditions for the culture as well as better reproducibility. An example of commercial use of cell-attachment surfaces is the Cytodex particles manufactured by Pharmacia wherein particles are coated with gelatin, making it possible to grow the same number of adherent cells in a much smaller volume of media than would be possible in dishes. The activity of these beads is, however, dependent upon the use of fibronectin in the growth medium in most cases. The cell-attachment polypeptide should provide a chemically defined coating for such purposes.

It is also anticipated that medical devices can be designed making use of such substrata to attract cells to the surface in vivo or even to promote the growing of a desired cell type on a particular surface prior to grafting. An example of such an approach would be the induction of endothelial cell growth on a prosthetic blood vessel or vacular graft, which is generally woven or knitted from polyester fiber, particularly Dacron fiber (a polyethylene terephthalate). Most types of cells are attracted to fibronectin and to this polypeptide, but endothelial cells and fibroblastic cells in particular are attracted to fibronectin and to this polypeptide. The latter point indicates the potential usefulness of this defined polypeptide in coating a patch graft or the like for aiding wound closure and healing following an accident or surgery. It is also indicative of its value in coating surfaces of a prosthetic device which is intended to serve as a temporary or semipermanent entry into the body, e.g. into a blood vessel or into the peritoneal cavity, sometimes referred to as a percutaneous device.

Although the invention has been described with regard to certain preferred embodiments, it should be understood that various changes and modifications, as would be obvious to one having the ordinary skill in this art, may be made without departing from the scope of the invention which is defined in the appended claims. Particular features of the invention are emphasized in the claims which follow.

What is claimed is:

1. The method of preparing substrata for the attachment of cells thereto, comprising deriving a polypeptide exhibiting a cell attachment activity having substantially the formula H-Ile-Gly-Gln-Gln-Ser-Thr-Val-Ser-Asp-Val-Pro-Arg-Asp-Leu-Glu-Val-Val-Ala-Ala-Thr-Pro-Thr-Ser-Leu-Leu-Ile-Ser-Trp-Asp-Ala-Pro-Ala-Val-Thr-Arg-Tyr-Tyr-Arg-Ile-Thr-Tyr-Gly-Glu-Thr-Gly-Gly-Asn-Ser-Pro-Val-Gln-Glu-Phe-Thr-Val-Pro-Gly-Ser-Lys-Ser-Thr-Ala-Thr- le-Ser-Gly-Leu-Lys-Pro-Gly-Val-Asp-Tyr-Thr-Ile-Thr-Val-Tyr-Ala-Val-Thr-Gly-Arg-Gly-Asp-Ser-Pro-Ala-Ser-Ser-Lys-Pro-Ile-Ser-Ile-Asn-Tyr-Arg-Thr-Glu-Ile-Asp-Lys-Pro-Ser-Gln-Met-OH and treating solid substrata having a surface to which cell attachment is desired with said polypeptide.

2. A method in accordance with claim 1 wherein said substrata is a synthetic resin material.

3. A method in accordance with claim 2 wherein said resin is nitrocellulose or polyester.

4. A method in accordance with claim 1 wherein said substrata is agarose.

5. A method in accordance with claim 1 wherein said substrata is long-chain polysaccharide.

6. A method in accordance with claim 1 wherein said substrata is glass.

* * * * *

UNITED STATES PATENT AND TRADEMARK OFFICE
CERTIFICATE OF CORRECTION

PATENT NO.   :   4,661,111
DATED        :   April 28, 1987
INVENTOR(S)  :   RUOSLAHTI et al.

It is certified that error appears in the above-identified patent and that said Letters Patent is hereby corrected as shown below:

IN THE ABSTRACT, line 14, delete "substrate" and insert therefore --substrata--.

Column 1, line 39, delete " hr" and insert therefore --Thr--.

Column 1, line 41, delete "Tyr- Arg" and insert therefore --Tyr-Arg--.

Column 2, line 36, delete "2982" and insert therefore --1982--.

Column 3, line 35, delete "Uppsala,," and insert therefore --Uppsala,--.

Column 4, line 38, after the first Thr insert --Val- --.

Column 4, line 40, delete "Thr- le-" and insert therefore --Thr-Ile- --.

Signed and Sealed this

Twenty-fifth Day of August, 1987

Attest:

DONALD J. QUIGG

Attesting Officer   Commissioner of Patents and Trademarks